US009404952B2

United States Patent
Druga et al.

(10) Patent No.: US 9,404,952 B2
(45) Date of Patent: Aug. 2, 2016

(54) CONDUCTIVITY MEASUREMENT OF FLUIDS

(71) Applicant: ASEPTIA, INC., Raleigh, NC (US)

(72) Inventors: Michael Druga, Raleigh, NC (US); John Alan Duff, Holly Springs, NC (US); Josip Simunovic, Raleigh, NC (US)

(73) Assignee: Aseptia, Inc., Raleigh, NC (US)

( * ) Notice: Subject to any disclaimer, the term of this patent is extended or adjusted under 35 U.S.C. 154(b) by 120 days.

(21) Appl. No.: 14/349,947

(22) PCT Filed: Oct. 4, 2012

(86) PCT No.: PCT/US2012/058738
§ 371 (c)(1),
(2) Date: Apr. 4, 2014

(87) PCT Pub. No.: WO2013/052657
PCT Pub. Date: Apr. 11, 2013

(65) Prior Publication Data
US 2014/0266267 A1    Sep. 18, 2014

Related U.S. Application Data

(60) Provisional application No. 61/543,078, filed on Oct. 4, 2011.

(51) Int. Cl.
*G01R 27/22* (2006.01)
*G01N 27/06* (2006.01)
(Continued)

(52) U.S. Cl.
CPC *G01R 27/22* (2013.01); *G01F 1/56* (2013.01); *G01F 1/708* (2013.01); *G01N 27/06* (2013.01); *G01P 5/20* (2013.01)

(58) Field of Classification Search
CPC ....... G01N 22/04; G01N 22/06; G01N 22/07; G01N 22/08; G01N 27/226; G01N 33/2823; G01R 27/22; G01F 1/56; G01F 1/708; G01P 5/20
See application file for complete search history.

(56) References Cited

U.S. PATENT DOCUMENTS 3,180,144 A    4/1965    Bennett
5,741,979 A *  4/1998    Arndt .................. G01F 1/74
                                                    324/639

(Continued)

FOREIGN PATENT DOCUMENTS

DE    10100773 A1    7/2002
DE    10332177 A1    9/2004

(Continued)

OTHER PUBLICATIONS

Sokolov, M. et al., Velocity measurements in slow flow by the Conductance-tracer method, Experiments in Fluids, Springer, Heidelberg, DE, vol. 9, No. 5, Jul. 1, 1990, pp. 252-256.

(Continued)

*Primary Examiner* — Son Le
(74) *Attorney, Agent, or Firm* — Merchant & Gould P.C.

(57) ABSTRACT

A product is provided into a first end of a conduit so that the product flows toward a second end of the conduit. The conduit may include a first pair of probes attached at a first location and a second pair of probes at a second location. The product's conductivity in the conduit at the first location is monitored using the first set of probes, and the product's conductivity at the second location is monitored using the second set of probes. An marker material is introduced into an entry port of the conduit so that the marker material flows with the product. The marker material's conductivity is different than the product's conductivity. At a first time, the first set of probes detects the conductivity of the product has changed due to the introduction of the marker material, and at a second time, the second set of probes also detects such change.

18 Claims, 9 Drawing Sheets

(51) Int. Cl.
*G01F 1/56* (2006.01)
*G01F 1/708* (2006.01)
*G01P 5/20* (2006.01)

(56) References Cited

U.S. PATENT DOCUMENTS

| | | |
|---|---|---|
| 6,467,358 B1 | 10/2002 | Nishi et al. |
| 2003/0203504 A1 | 10/2003 | Hefti |
| 2006/0158192 A1 | 7/2006 | Beaulieu et al. |
| 2007/0061093 A1* | 3/2007 | Angelescu .......... E21B 47/1015 702/100 |
| 2008/0160623 A1* | 7/2008 | Su ........................ G01F 1/56 436/94 |
| 2012/0068723 A1* | 3/2012 | Sullivan ................ G01N 27/07 324/654 |

FOREIGN PATENT DOCUMENTS

| | | |
|---|---|---|
| FR | 2909764 A1 | 6/2008 |
| GB | 1088773 A | 10/1967 |
| WO | WO 00/45133 A1 | 8/2000 |
| WO | 2007009097 A1 | 1/2007 |

OTHER PUBLICATIONS

European Patent Office, Extended Search Report for Application No. 12838844.4 mailed on May 29, 2015, 8 pages.

Jan. 24, 2013 International Search Report issued in International Patent Application No. PCT/US2012/058738.

Jan. 24, 2013 Written Opinion issued in International Patent Application No. PCT/US2012/058738.

* cited by examiner

CONDUCTIVITY MEASUREMENT OF FLUIDS

CROSS REFERENCE TO RELATED APPLICATION

This application claims priority under to co-pending U.S. Provisional Patent Application No. 61/543,078 filed on Oct. 4, 2011, the disclosure of which is incorporated herein by reference in its entirety.

BACKGROUND

The effectiveness of thermal processing technologies may be dependent upon the conductivity of the product being processed.

Currently there is no way to accurately measure the conductivity across the product when the product is disposed within a cavity. For example, if a fluid is flowing in a tube, there is no way to accurately measure the conductivity of such product flow axially along the product, over time and over different frequency ranges.

SUMMARY

According to one aspect of the present invention, a system may be based on pairs of probe tips (e.g., 13 mm diameter "Low Profile" probe tips) combined with conductivity measurement hardware that applies a voltage at a specified frequency across the pairs of probes to measure the conductivity between those probes. Data acquisition hardware and analysis software may record this data and provide real time feedback to the user as well as historical trending capability.

According to another aspect of the present invention, multiple pairs of conductivity sensors can be arranged radially at the same location, or axially at different locations, in order to measure the conductivity variations within the flow profile.

According to another aspect of the present invention, by introducing a known quantity of a different conductivity material (e.g., salt solution) at a specific location in the process, then measuring when that same "spike" of fluid passes subsequent downstream locations in the process, the residence time as well as the residence time distribution for each section of the process can also be determined.

The system can serve multiple purposes: (1) as a basis to implement a method for determination of residence times of fluid products in a continuous process by the injection of a salt solution; (2) as a method to determine approximate overall conductivity for a cross section of fluid in a continuous process; (3) to determine the product flow profile within a pipe section in a continuous process to detect product separation in real time; (4) to detect changes in the product properties and prevent over or under processing by tracking changes in the conductivity over time; (5) to determine residence times and residence time distributions of the carrier fluid for heterogeneous (particle-containing) products; (6) to determine the residence times and residence time distributions of product at different cross-sectional locations within the flow profile (i.e. in the center of flow vs. the edge of flow at the—at the interface with the tube walls, top of the tube vs. bottom of the tubes for substantially horizontal flow regimes; (7) to measure the residence time and residence time distribution of individual real food or biomaterial particles saturated with an ionic (i.e. sodium choride) solution and determination of times of passage between staggered probe pairs by detecting the time of localized increase in conductivity caused by the passage of salt-saturated particles; (8) to measure the residence times and residence time distributions of simulated food (fabricated from polymers/insulating materials), preferably sensor-carrying particles via determination of times of passage between staggered probe pairs by detecting the time of localized decrease in flow cross-sectional conductivity caused by the passage of polymer/insulator particles; (10) determination of whole product (combination of both fluid and solid components) residence times and residence time distributions by rapidly and briefly heating a small product product volume using an advanced thermal (volumetric) heating method (such as microwave, ohmic or radio-frequency, thereby causing a localized, temperature-dependent "spike" in the conductivity of the small volume of heated product and detecting and recording the resulting localized increase in conductivity at downstream probe pair locations and (11) determination of potential changes in flow regime (e.g. from laminar to turbulent and/or from turbulent to laminar) of the product in individual system segments by comparing the temporal conductivity profiles between subsequent probe pairs surrounding individual processing system segments. The implemented analyses/comparisons could vary from the comparisons of curve widths (time of initial detection to time of last detection for individual), areas under the curve, peak heights and curve distribution parameters such as temporal distribution between curve tails and curve center, quantification of asymmetry—comparisons of the leading tail end of the curve vs. the trailing end tail of the curve etc.

According to one aspect of the present invention, a method includes: providing a product into a first end of a conduit so that the product flows toward a second end of the conduit, wherein the conduit comprises an interior cavity and has a first pair of probes attached at a first location and a second pair of probes at a second location, the first and second locations being separate from each other and being between the first and second ends; monitoring the conductivity of the product flowing in the conduit at the first location using the first set of probes; monitoring the conductivity of the product flowing in the conduit at the second location using the second set of probes; introducing a marker material into an entry port so that the marker material flows with the product toward the second end, the marker material comprising or causing a conductivity that is substantially different than the conductivity of the product; detecting, at a first time, that the conductivity at the first set of probes at the first location has changed due to the introduction of the marker material; and detecting, at a second time, that the conductivity at the second set of probes at the second location has changed due to the introduction of the marker material.

According to another aspect, a system may include a conduit for carrying a product, a first set of probes and a second set of probes. The conduit may include a first end, a second end, a body defining a first pair of apertures at a first location and a second pair of apertures at a second location, wherein the first and second locations are separate locations and are in between the first and second ends, an interior cavity configured to receive the product so that the product flows from the first end toward the second end; and an entry port for receiving the marker material which is configured to flow with the product when introduced. The first set of probes disposed in the first set of apertures at the first location, wherein the first set of probes is configured to measure conductivity of the product located at the first location, wherein the first set of probes is further configured to detect, at a first time, that the conductivity at the first location has changed due to the introduction of the marker material. The second set of probes is disposed in the second aperture, wherein the second set of probes is configured to measure conductivity of material located at the second location, wherein the second set of probes is further configured to detect, at a second time, that the conductivity at the second location has changed due to the introduction of the marker material.

According to yet another aspect, a method may include providing a conduit comprising a first set of probes and a second set of probes, wherein each of the first and second set of probes are spaced from each other along a length of the pipe, wherein the first set of probes oppose each other and are orientated radially about the pipe at a first radial position, and wherein the second set of probes oppose each other and are orientated radially about the pipe at a second radial position, wherein the first radial position is different from the second radial position; measuring, using the first set of probes, conductivity of a fluid within the conduit when the fluid is at the first set of probes; measuring, using the second set of probes, conductivity of the fluid when the fluid is located at the second set of probes within the conduit; and determining homogeneity of the fluid based on the measurement of the conductivity of the fluid at the first and second set of probes

BRIEF DESCRIPTION OF SEVERAL VIEWS OF THE DRAWINGS

Embodiments of the present invention is further described in the detailed description which follows in reference to the noted plurality of drawings by way of non-limiting examples of embodiments of the present invention in which like reference numerals represent similar parts throughout the several views of the drawings and wherein.

DETAILED DESCRIPTION OF SOME EMBODIMENTS

Figure 1:
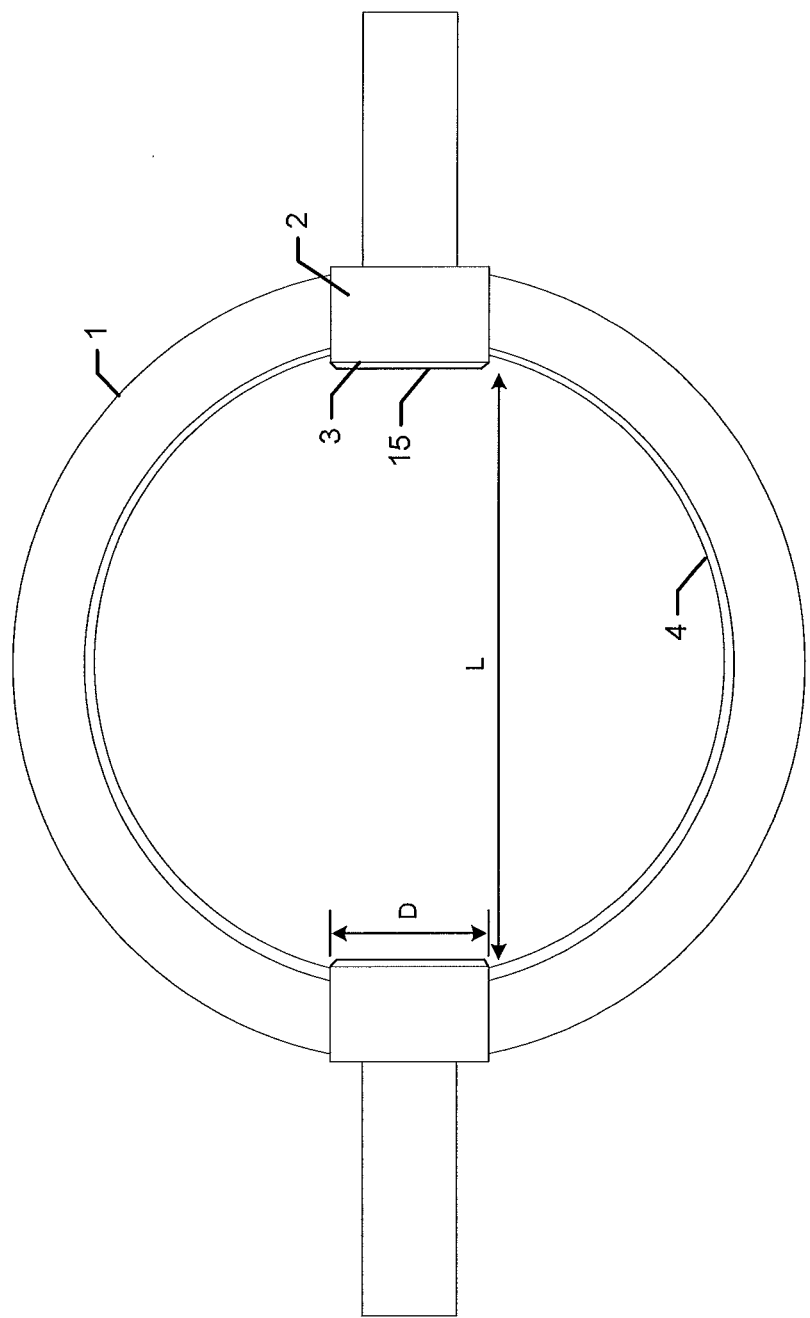
FIG. 1 illustrates a cross-section of a part of a system for measuring of product in the pipe accordance with an embodiment of the present invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

As used herein, a class may define an abstract characteristic of a thing or object, such as a group of code or instructions for performing a particular operation or function. The abstract characteristics may include characteristics of the thing or object, for example attributes, fields or properties, behaviors, such as functions or methods that can be performed by the class. An object is a particular instance of a class. The set of values of the attributes of a particular object is the state of the object. The object includes the state and the behavior that is defined in the object's class. A method is an object's abilities or functions the object can perform.

Various embodiments of the present disclosure will now be described. The conductivity of a product flowing in a conduit (e.g., a pipe) may be desired to be accurately measured. It should be understood that the term "product" refers to material within the conduit, such as a fluid. The amount by which a product conductivity varies radially across the product flow (e.g., axially along the product), over time and over different frequency ranges has a direct impact on how the electrical energy is distributed and absorbed, and hence how evenly the product is processed. Any measurement of process parameters in continuous flow systems may be performed with minimal disturbance to the product flow, as any disturbance may potentially affect the product mix, and hence the parameter distribution within the flow.

To measure the conductivity in the conduit or pipe, two probes may be inserted into a pipe at a 180 degree angle according to some embodiments. While the present disclosure illustrates the angle between the two probes as 180 degrees, it should be understood that other embodiments allow the two probes to be inserted into a pipe at an angle other than 180 degrees from one another, such as 90 degrees, 110 degrees, etc.

Regardless, the two probes may be located in a plane that is substantially perpendicular to the longitudinal axis of the pipe. A voltage differential may then be applied across the two probes to induce a current. This current is then measured allowing the conductivity of the product to be measured through the standard equation:

$$G=I/E$$

Where G is the measured conductivity given by the current, I (in Amps), is divided by the Voltage, E, in Volts. The basic unit of conductivity is the siemens (S).

The specific conductivity is denoted by C where:

$$C=G\times(L/A)$$

The unit of specific conductivity is (S/cm) which is the product of measured conductivity and the electrode cell constant to compensate for cell geometry. Variable L is the shortest length between the tips of each probe as illustrated in FIG. 1. Variable A is the surface area of the conductive face of each probe, where the face of a probe includes the surface of one probe facing the surface of another probe. The conductivity measurement system may be adapted to any diameter pipe by adjusting the supply voltage to ensure measurable current levels.

According to FIG. 1, the surface area of the probe face can be found by the following equation:

$$A=\pi r^2, r=\tfrac{1}{2}D$$

In the event that the probe face is circular whereby r is the radius of the circular face and D is the diameter of the circular face.

It should be understood that the probe face may be any other shape, such as square, and as such the area of the face of the probe is calculated according to the face shape. For example, if the probe face is square, the area of the probe face is square of the length of each side of the face.

FIG. 1 illustrates a cross-section of a part of a system for measuring of product in the pipe accordance with an embodiment of the present invention. The system may include a conduit (e.g., a pipe 1) and a pair of probes 2. The pair of probes are therefore opposingly disposed in the conduit so that they face each other and are disposed in a plane that is perpendicular to and intersects a longitudinal axis of the conduit (which would be a line along the center of the interior cavity of the conduit in FIG. 1).

The material of the pipe 1 may be any material, such as stainless steel for food applications, non conductive food grade materials such as PTFE Teflon, or carbon steel or PVC for non-food applications. In one embodiment, the material of the pipe 1 can be modified with an insulating interior coating to enhance detection resolution.

The system may further include an insulating barrier between a conducting surface 3 of the probe and any potential conducting surface other than the product being measured.

Figure 7:
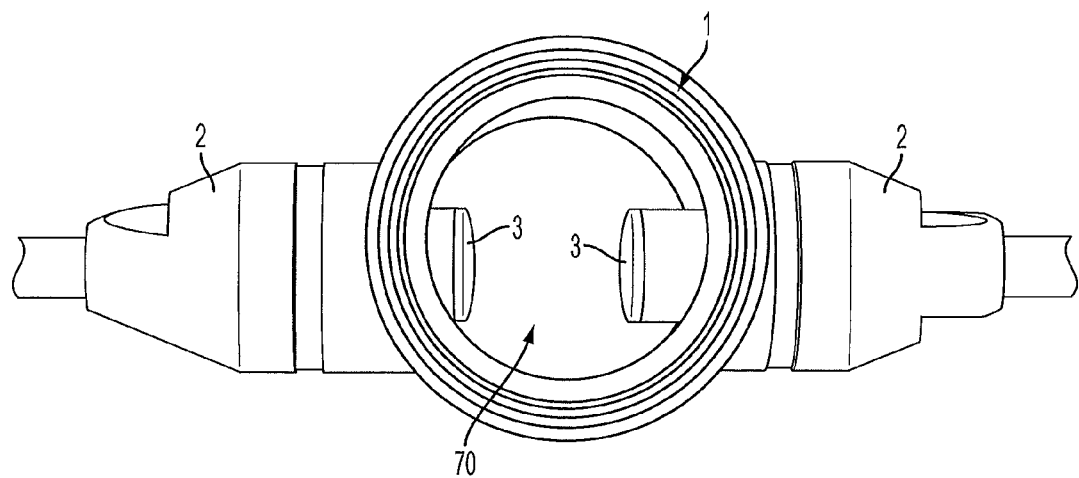
FIG. 7 illustrates a cross section of the pipe with sensors of FIG. 6, according to an embodiment.
Figure 8:
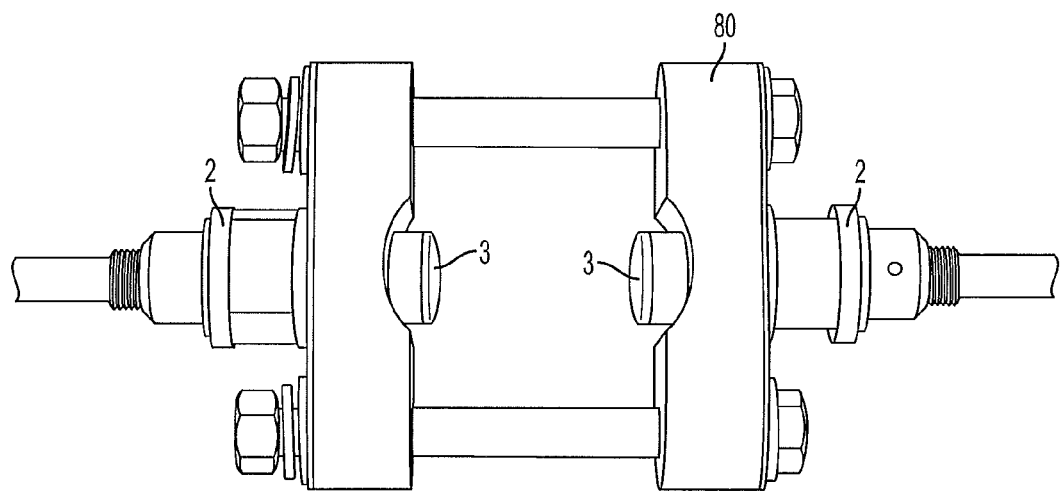
FIG. 8 illustrates a sensor mounting bracket with sensors according to an embodiment.

Each probe has a conducting surface 3 which contacts the fluid within the pipe 1. The conducting surface 3 may be the face of the probe as seen in FIGS. 7 and 8. The conducting surface 3 may be the stainless steel portion of the probe within the pipe. That metal face of each probe may be surrounded by a food safe plastic material to fasten to the pipe such that no conductive components of the probe touch the pipe, thereby electrically insulating the conductive probe face from other conductive objects in the pipe (including the inner wall of the pipe).

In one embodiment, the probe may have a circular flat tip. It should be understood that the probe tip may be any other shape, such as square, dome-shaped, pointed, or any other shape.

The system may further include an insulating barrier 4, as illustrated in FIG. 1, whereby the insulating barrier 4 is located between the probe conducting surface 3 and any potential conducting surface other than the product being measured. For example, the insulating barrier 4 can be a plastic liner adjacent to the wall of the pipe 1 or a PTFE Teflon coating along the interior of pipe 1. This ensures that the current flow within the pipe will be between the conductive surfaces 3 of the probes 2.

Figure 2:
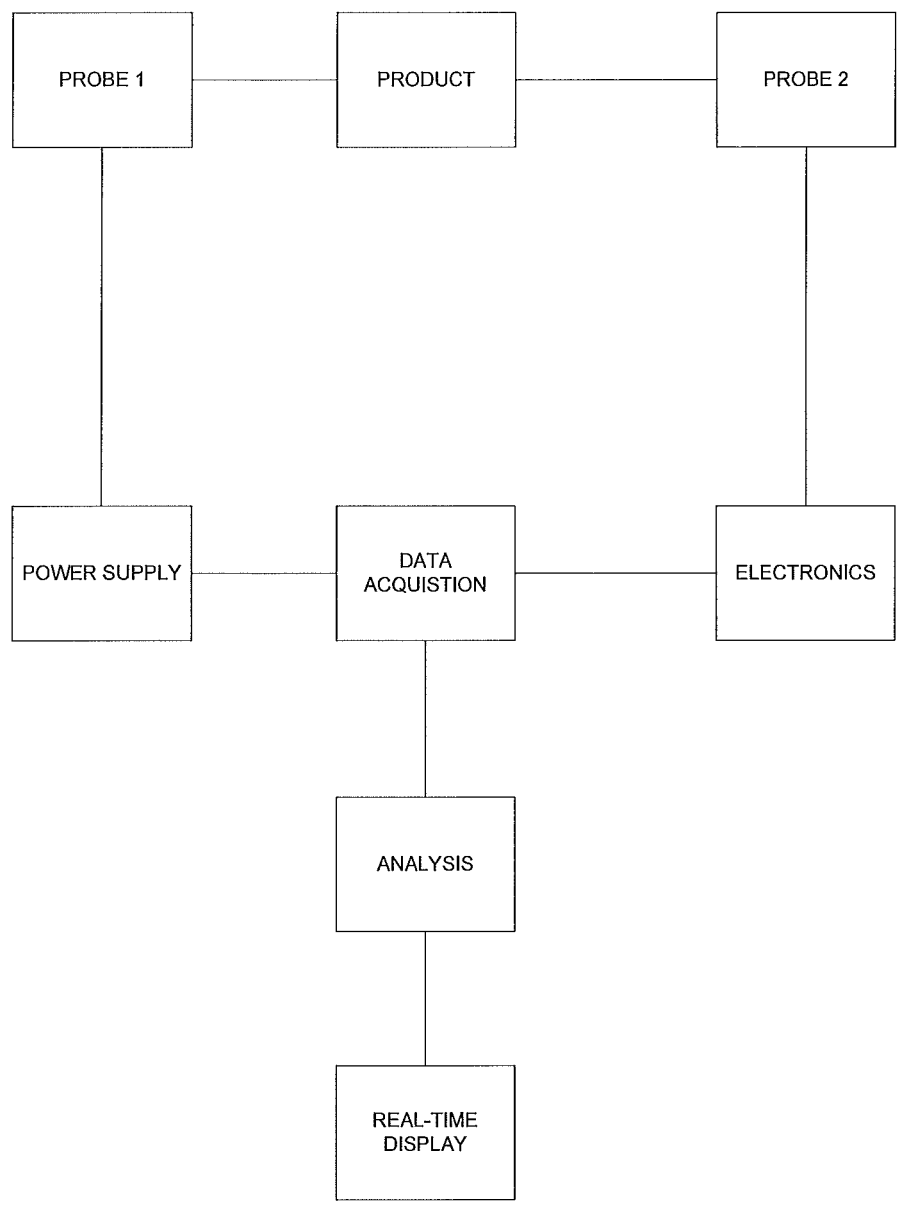
FIG. 2 is a block schematic diagram of an example of a system for multiple identity recognition in accordance with another embodiment of the present invention.

As shown in block diagram in FIG. 2 the two probes (Probe 1 and Probe 2) may be separated by a space within the pipe 1 where the product is located therebetween. As stated above, the product can be a fluid which may be completely conductive (or at least partially conductive). The space in between the two probes and the distance between the probes may be proportional by the diameter of the pipe 1 since the probes 2 may be orientated on opposing sides proportional by the diameter of the pipe 1 since the probes 2 may be orientated on opposing sides. As such, the distance and space between the probes 2 may be determined by the diameter of the pipe.

Each probe has a probe tip which accesses the interior cavity of the pipe 1 through an aperture of the pipe so that the probe tip can contact product located within the interior cavity of the pipe 1 according to some embodiments. In one embodiment, the probe tips may be positioned so as to minimize disruption of the product flow and therefore they may be as close to the walls of the pipe 1 as possible so that the probe tips do not substantially protrude into the interior cavity of the pipe.

The probe tips are spaced a distance apart from each other. For example, in one embodiment, a standard 2" diameter pipe would have a distance between probes of approximately 1.75". The probes may be aligned on opposite sides of the pipe at 180 degrees apart such that they are facing each other in a direct line.

A power supply is connected with the probes and provides a potential difference between the set of probes to induce the current through the product which is disposed between the probes. The power supply may supply AC voltage and may be a transformer to step a standard 110 Volt, 60 Hz source down to 5 volts at 60 Hz or a more complex power supply with variable frequency output to take measurements at specified frequencies. The voltage shall be kept as low as possible to minimize any fouling or interference with the processing. An installation may use the 60 Hz supply from the grid stepped down through a transformer to 5 $V_{AC}$. This constant power source shall be maintained at a specific voltage and frequency any time the sensor is active. An electrical circuit is then created between the two probes utilizing a fixed resistor to limit the maximum current. The resulting current is measured and recorded through a data acquisition device wired in the circuit to measure current directly or more commonly the data acquisition device measures the voltage drop across a current sense resistor with a known value. In some embodiments, a high tolerance ceramic resistor, such as a 5 Ohm ceramic resistor with a tolerance of 1% or less may be used to maximize sensitivity and set the voltage drop range between 0-100 mV for the full range of conductivity between open air and direct short.

Figure 10:
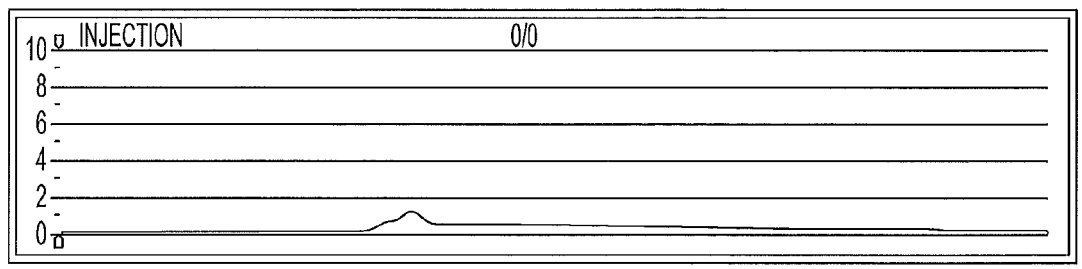
FIG. 10 illustrates a graph of conductivity over time resulting from measurements taken from the probes, according to an embodiment

A computer may be connected to the data acquisition device via Ethernet or USB to record, analyze and display the results such the results illustrated in FIG. 10 where a histogram shows the relative conductivity over a period time. FIG. 10 illustrates a computer software program display graph of conductivity over time where, in this example, conductivity is displayed in a unitless scale of 0-10 where 0 is the lowest reading or open circuit and 10 is the highest reading or short circuit, and thus displaying the full detection range of the system according to an embodiment. This allows real-time feedback of the conductivity of the product located between the set of probes in a continuous flow process. Each pair of probes with corresponding circuitry is considered a single measurement point.

As described below, multiple pairs of probes may be used and thus, multiple measurement points may be obtained.

Exemplary Application Using Multiple Measure Points:

By installing multiple measurement points (each measurement point being a set of probes configured to take conductivity reading as discussed above) at a known distance from each other a conductive fluid may be introduced in the product stream to allow the system to measure the residence time of the fluid. The residence time of the fluid is a parameter in food processing and may be defined as the time the product spends in a particular process area or zone (e.g., the area or zone may be defined as a distance between two points, such as between two sets of probes). The user may know of how long the product spends within a heating section of a continuous process thus revealing the residence time within that heated section.

Figure 3:
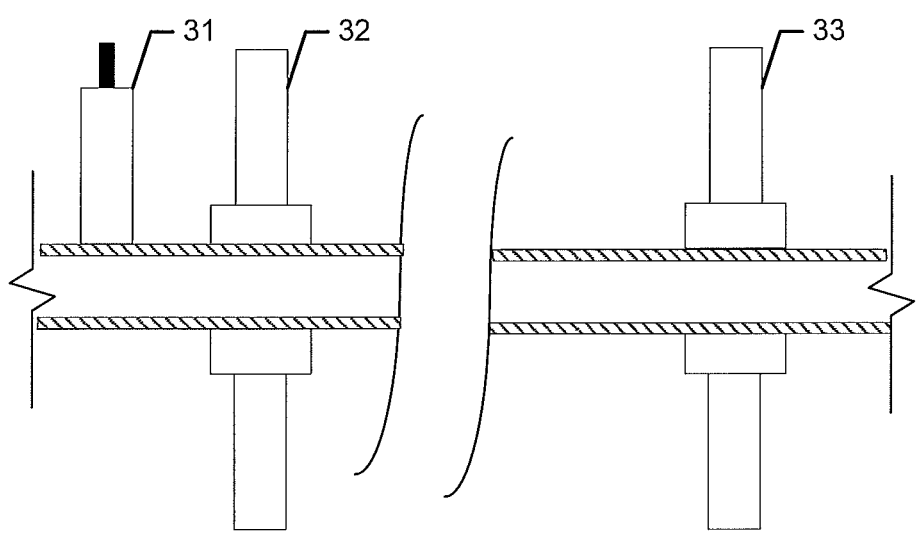
FIG. 3 shows a side view of a pipe having product flowing through the pipe, according to one embodiment.
Figure 11:
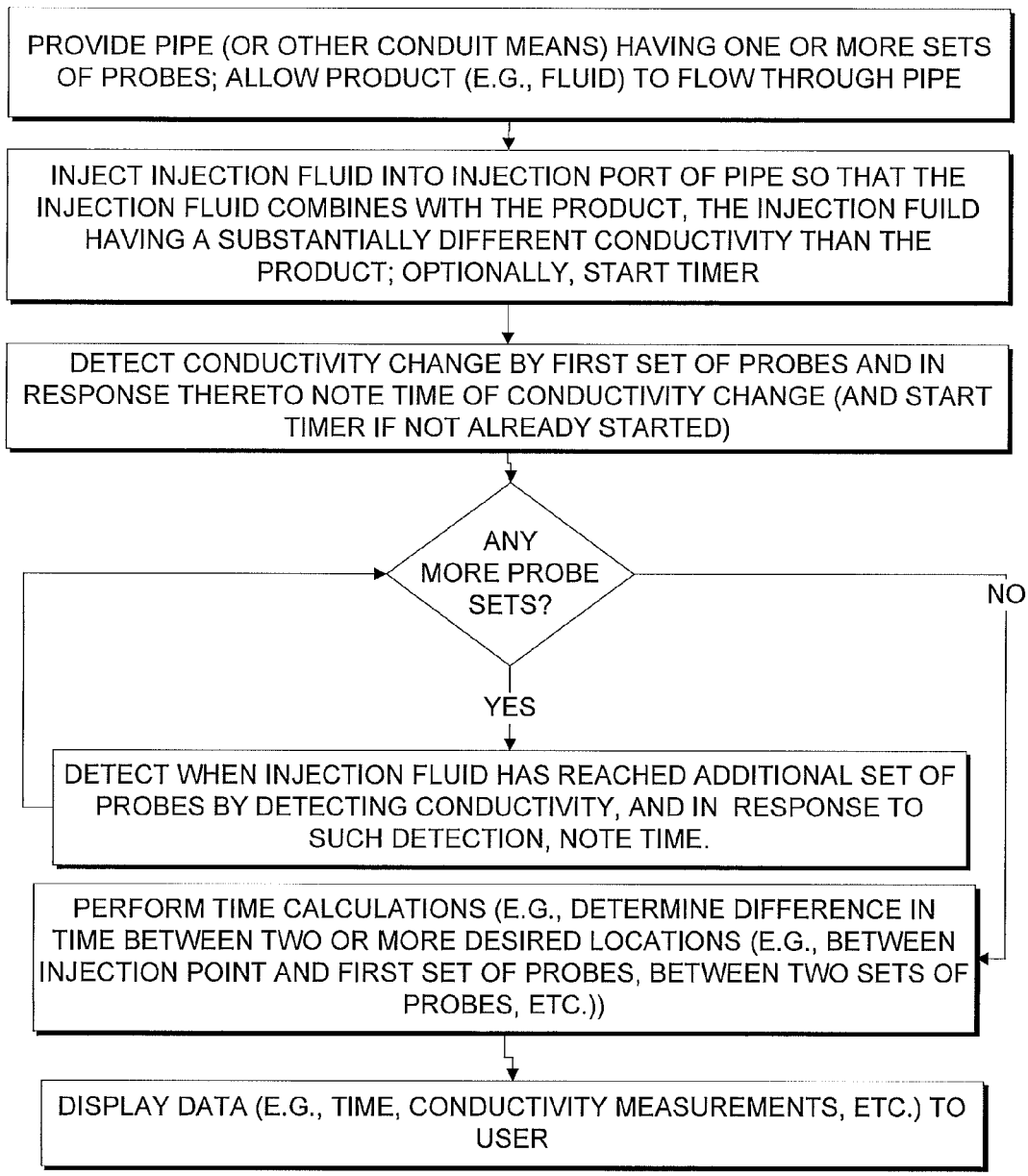
FIG. 11 illustrates a method of using conductivity measurement of fluids, according to one embodiment.

It should be understood that the residence time may not be the only analysis determined using the present invention. For example, the present system may use data measured by a plurality of probes to compare multiple time and conductivity points (i.e. the conductivity curve) at individual probe locations along the conduit to determine flow regimes and implement the results to pasteurization and sterilization protocols Another control parameter may be the amount of time the product spends in certain sections of pipe known as the hold tube section. Again, the residence time of the liquid product in this zone may be measured by the time delay between detection at two points, one immediately before and one immediately after a zone of interest. This is illustrated by FIGS. 11 and 3. FIG. 11 illustrates how a method of determining a residence time and FIG. 3 shows a cross-section side view of a pipe (where the cross-section is taken along the longitudinal axis of the pipe) having product flowing through the pipe and having a two probes attached to the pipe at different locations, according to one embodiment.

In FIG. 3, there are two sets of probes 32, 33 and an introduction port 31, all of which are connected with a conduit or pipe which allows fluid to flow therein. Notably, the first set of probes 32 and/or second set of probes 33 may be substantially the same as the set of probes previous discussed, and thus, the probes may be configured to be located on opposing sides of the pipe and configured to access the interior of the pipe. The two sets of probes are each independently operable and can take measurements of conductivity between each of the sets of probes. For example, the first set of probes take conductivity measurements the first set of probes (disposed at a first location in the pipe), and the second set of probes (disposed at a second location in the pipe) takes conductivity measurements between the second set of probes. The two sets of probes are also spaced a distance from each other (measured between the first and second locations) and such spacing is along the longitudinal axis of the pipe 1.

In FIG. 3, a material with significantly different conductivity than the product (hereinafter "the marker material") may be introduced into the introduction port 31 so that the introduced liquid is introduced into the product flow. According to some embodiments, the introduced marker material could be any liquid or solid with a conductivity significantly different (e.g., different in the sense that the conductivity change may be detected by the probes) from the flowing product, such as a sodium chloride solution, potassium chloride solution, deionized water, salt-infused particulate food or biomaterial, simulated food pieces fabricated from a substantially insulating material etc. so long as after the introduced material has been entered into the product flow, the conductivity of the combination is different than the conductivity of the product alone.

According to another embodiment, the introduced marker material can also be defined for the purposes of this application as a quantity or spike of thermal or electromagnetic energy resulting in a significant brief increase in temperature within a small flowing volume of productalready in the conduit—and a related increase in product conductivity within the same flowing volume of product in the conduit. For example, instead of i a fluid or solid, the marker material may be an application of thermal or electromagnetic energy into the product flowing in the conduit.

In another embodiment, the marker material may be product not flowing in the conduit (but the same type of material as that flowing in the conduit) which is thermally increased and then introduced into the conduit to mix with the same type of product already flowing in the conduit. In this regard, the marker material is the same material flowing in the conduit, but has a different conductivity than the product in the conduit due to having added thermal energy.

It should be understood that the introduced materials can be any material, such as a liquid, solid or intangible item. For example, the marker material can be pre-treated (salt-solution immersed) pieces of real food or biomaterial, simulated food or biomaterial particles fabricated of insulating (polymer) materials, as well as short bursts of thermal energy (via microwave, ohmic or radio frequency heating) which may result in brief, localized temperature and conductivity increases in small product volumes. The marker material may be the same material as that disposed in the conduit but has a different temperature than the material flowing in the conduit.

After the marker material is introduced at the introduction port 31, the corresponding difference in the conductivity is detected by a first set of probes 32 (as previously discussed) by the analysis software. This detection causes a timer to start within the software to begin tracking (e.g., timing) the introduction to the next configured point. This time is marked in the analysis software on the computer connected to the data acquisition device. At this point, the introduction solution is detected again at the next location (e.g., the second set of probes 32) and the time is marked in the analysis software. The analysis software then calculates the time offset between the two measurement points (e.g., between the first set of probes 32 and the second set of probes 33, between the introduction point 31 and the first set of probes 32, between the introduction point 31 and the first set of probes 32, etc.) to determine how long the fluid was between the two points/locations thus determining the residence time of the fluid.

For example, after introduction, when the conductivity difference is detected at the first set of probes 32, the timer begins. The timer will make a note of this time. Then when the conductivity change is detected at the second set of probes 33 (i.e., the conductivity measured changes by a threshold amount), this time is also noted. This allows a time to be determined from the introduction point 31 to the first set of probes 32, between the first set of probes 32 and second set of probes 33, and/or between the introduction point 31 and the second set of probes 33. It should be understood that the system may determine the total time between the first and second set of probes. However, it should be understood that any time can be determined between any two locations. For example, the timer may note the time that the marker material was introduced and the time it takes the marker material to reach the first and/or second set of probes and to perform difference calculations between any of the desired locations. It should also be noted that the timer may be continuous and the probe sets readings may also be continuous to allow the software or user to determine time between two points.

The above exemplary methods are illustrated generally by FIG. 11. FIG. 11 illustrate some embodiments of methods of measuring conductivity of fluids or product and using such measurement in performing various calculations, as is discussed above. As illustrated in FIG. 11, a pipe (or other conduit) is provided having one or more sets of probes and allowing product to flow in the interior cavity of the pipe, as previously discussed. The marker material (also referred to herein and/or in the Figures as "injection fluid") is then introduced into the introduction port (also possibly referred to herein or in the Figures as "injection port") of the pipe so that the marker material combines with the product. As previously mentioned, such combination results in an overall conductivity that is substantially different than the product alone (i.e., not combined with the marker material). Next, such conductivity change or difference is then detected by a first set of probes and in response to such detection, a timer may be started. It should be understood that the timer may be started at any moment, such as when the marker material is introduced into the pipe, etc. Next, it is determined whether, along the longitudinal length of the pipe, there are any more probe sets (in addition to the first set of probes) that have not yet detected the conductivity change or the marker material/product combination has not reached. If not, then the method may determine the time between two locations, such as the introduction point and the first set of probes. However, if there is another set of probes that has not yet detected the marker material/product mixture, then the method detects when the marker material has reached the additional set of probes (located a distance along the longitudinal length of the pipe from the first set of probes) by measuring the difference in conductivity between the product and the marker material/product mixture. In response to detecting that the marker material and product combination has reached the additional set of probes, the method may note the time, and perform any time calculations. For example, the method may perform how long the marker material and product combination took to flow from the first set of probes to the additional set of probes. The method then repeats the above steps for each additional set of probes until all sets of probes have detected the marker material /product mixture. The resulting data (e.g., time, conductivity measurements, etc.) can be displayed to the user, such as that shown in FIG. 10.

Figure 12:
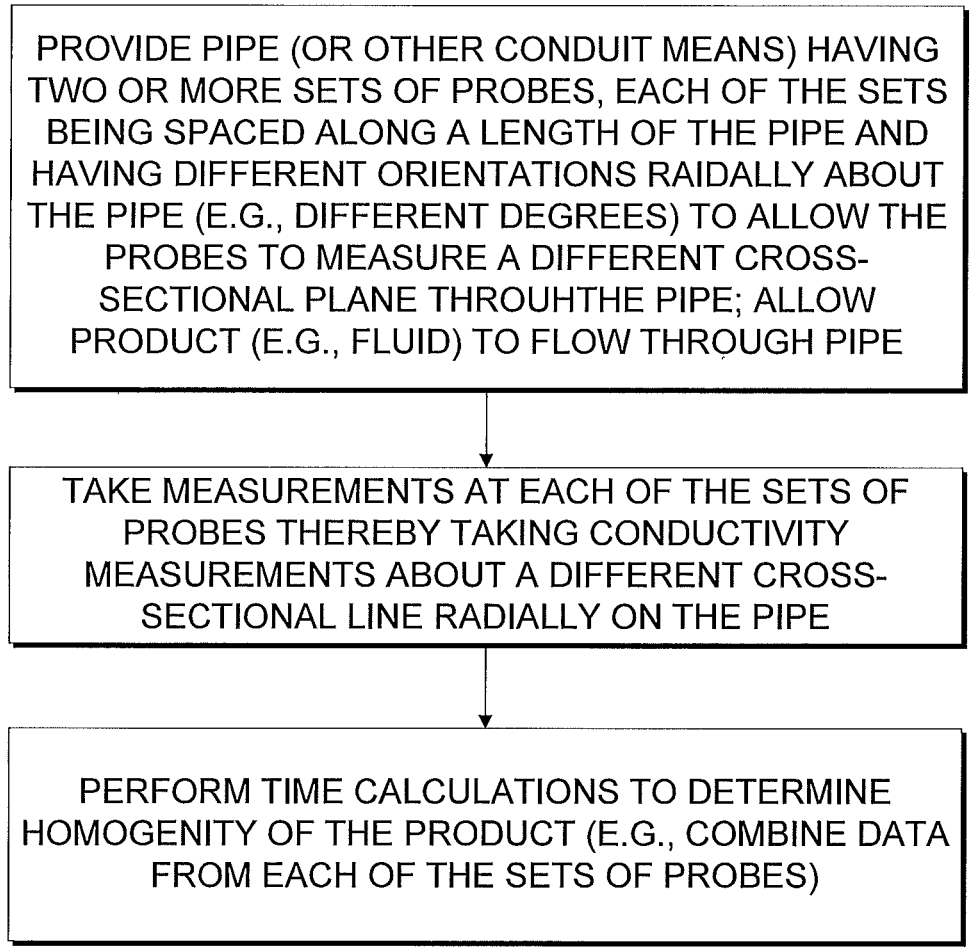
FIG. 12 illustrates a method of using conductivity measurement of fluids, according to another embodiment

Exemplary Application:

By installing multiple measurement points in succession with a different orientation, the product flow profile may be determined. The product flow profile will determine if the product is settling on the bottom of the pipe, floating to the top of the pipe, or mixing evenly throughout the flow. This can be a measurement point for sensitive processes and help processors determine if changes are needed to their formulation to maximize product quality. This would also be an indication of how well an inline mixer is performing with regards to product mixing. FIG. 12 illustrates the embodiments presented in this section.

Figure 4C:
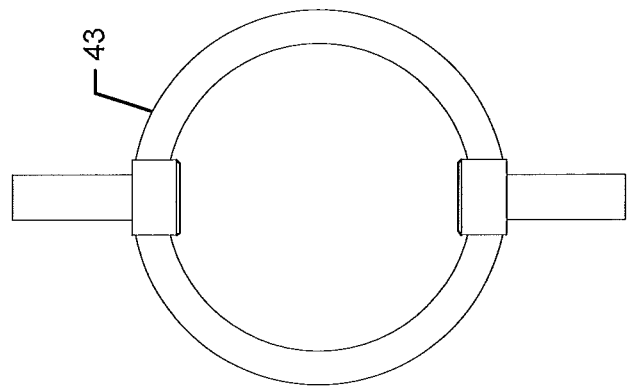
FIG. 4 illustrates a cross sectional views of positions of probes on a pipe, according to various embodiments.
Figure 4B:
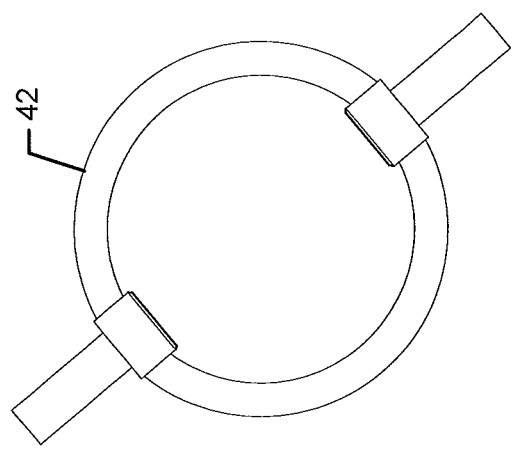
Figure 4A:
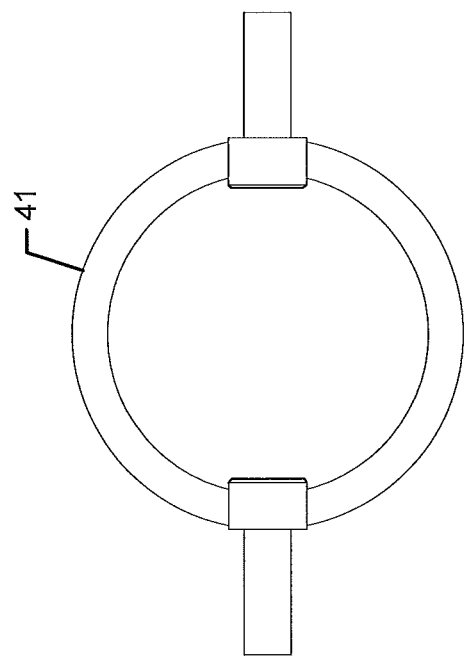

In some embodiments, this measurement may be achieved by placing multiple measurement points (each point may include a pair of probes) along the pipe within a close proximity (e.g., no more than 1 foot apart) along the length of the pipe and each point must be within the same length of straight pipe uninterrupted by any fittings, elbows, or restrictions in the pipe. Each measurement point may be focused on a different area of the flow radially and each point shall be configured in the software accordingly. This may be done by placing opposing probes about the pipe, as illustrated in FIG. 4 (collectively FIGS. 4A, 4B and 4C). In FIG. 4A, a pipe/probe configuration 41 illustrates the probes are placed at 90 degrees and 270 degrees around the pipe, which will measure the conductivity along the horizontal cross section of pipe. In FIG. 4B, a pipe/probe configuration 42 illustrates the probes may be placed at 150 degrees and 330 degrees around the pipe, which measures a combination of vertical and horizontal conductivity profiles. In FIG. 4C, a pipe/probe configuration 43 illustrates the probes are placed at 0 degrees and 180 degrees around the pipe, which measures the conductivity along the vertical cross-section of the pipe. It should be understood that the present disclosure does not limit to actual location of the probe configurations, as each set of probes may be placed at any location around the pipe. Regardless, each placement of the probes allows the probes to determine the conductivity at different orientations respectively within the product flow profile since a significantly different conductivity reading by one of the measurement points with respect to another point indicates that the product flow is not homogenous along a given crosssection of the pipe. By obtaining multiple cross-sectional measurements, the software may then analyze the difference between these measurements and make a determination of how much product separation is occurring. In an ideal process, one may desire a homogenous profile and therefore all measurement points should read the same in a properly mixed product. Any deviation between the conductivity readings will identify a potential problem (i.e., a nonhomogenous mixture along a cross-section of the pipe) such as product settling at the bottom (or side) of the pipe or particulates floating along the top (or other side) of the pipe. Each component within a given product formulation will have different dielectric characteristics and therefore any concentration of a given ingredient or product component at one portion of a given cross-section of the pipe will alter the conductivity at the location of the concentration, typically the top or bottom (or sides) of the pipe. This floating or settling yields significantly different readings between the conductivity in the horizontal and vertical cross sections of a given section of the pipe as the vertical cross-section of the pipe section would read both the top and the bottom of the pipe whereas the horizontal cross-sections would exclude any product settling at the top or bottom of the pipe.

Figure 5:
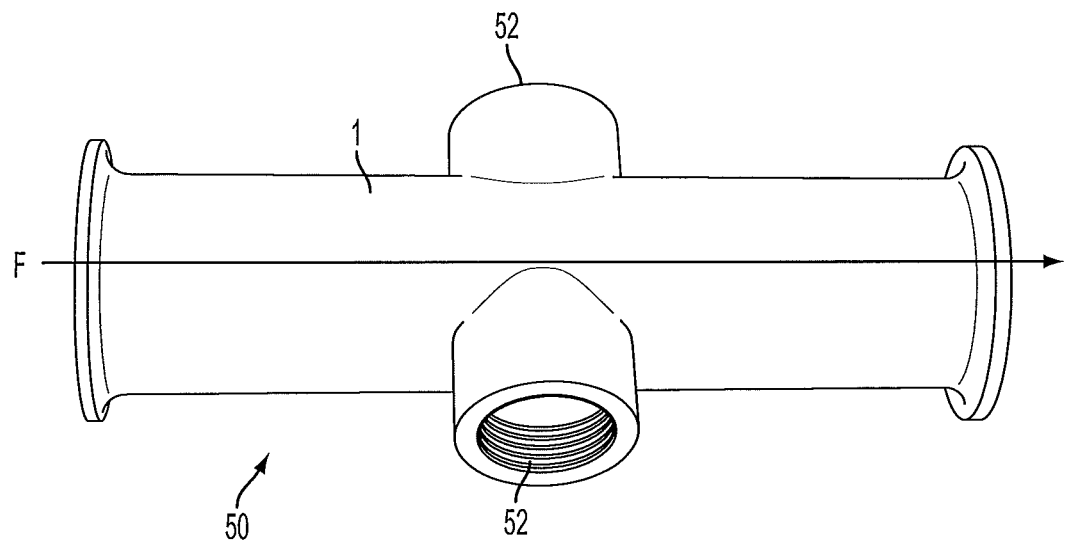
FIGS. 5 and 6 illustrate a saddle welded pipe section without sensors and with sensors, respectively, according to an embodiment.
Figure 6:
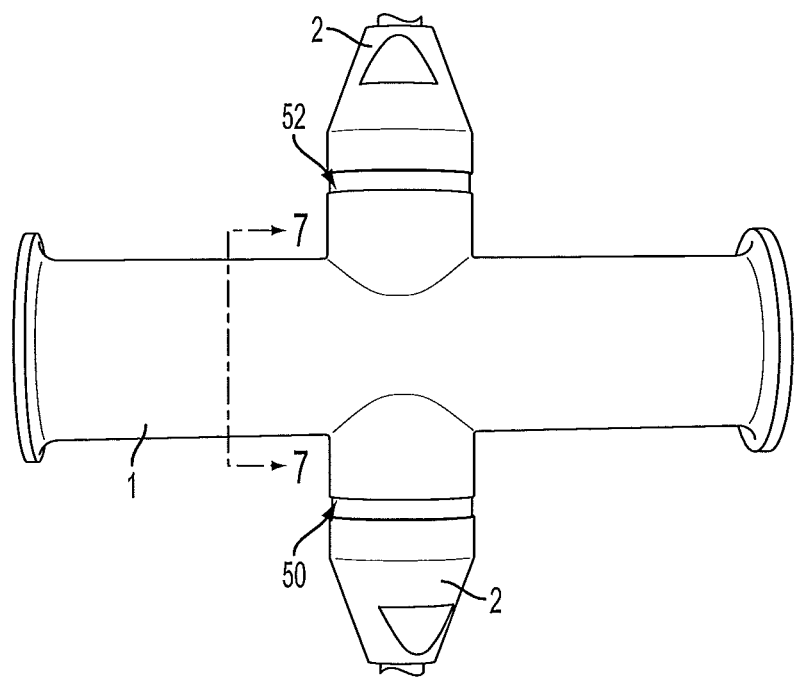
Figure 9:
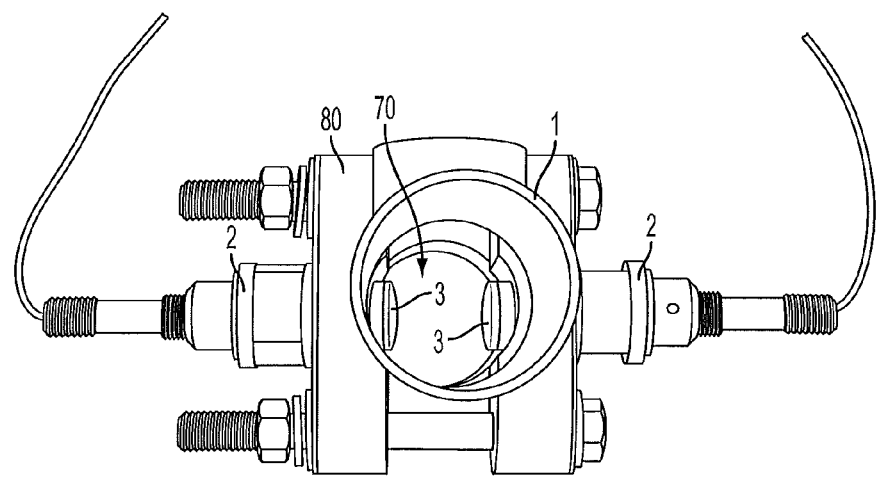
FIG. 9 illustrates the sensor mounting bracket with sensors of FIG. 8 attached to a pipe according to an embodiment.

FIGS. 5-9 illustrate various configurations for installation of the system, according to various embodiments. FIGS. 5 and 6 illustrate a saddle-welded pipe section 50 having ports 52 without probes and with probes 2, respectively, according to an embodiment. FIG. 7 illustrates a cross section of the pipe with probes of FIG. 6, according to an embodiment. FIG. 8 illustrates a probe mounting bracket with sensors according to an embodiment, and FIG. 9 illustrates the probe mounting bracket with sensors of FIG. 8 attached to a pipe.

As illustrated in FIGS. 5-7, the saddle welded connection fittings 50 have apertures ports on opposing sides of a base pipe to allow for probes to be attached to directly on a section of the pipe so that the probes can access an interior cavity 70 of the pipe. FIG. 5 illustrates a top view of the saddle welded connection fittings 50 with no sensors (e.g., probes) attached to the pipe 1. It should be understood that when the fitting 50 is connected to a system (not shown) the product flow will be as shown by the directional path F. FIG. 6 illustrates the same top view that FIG. 5 illustrates except with the probes 2 attached to the ports on the opposing sides of the base pipe.

FIG. 7 is a side view of the saddle welded connection fittings 50 with probes 2 attached to the ports 52. This illustrates that the probes 2 are connected so that a portion 3 extends to a interior cavity 70 of the pipe 1 so that when fluid flows, the probe tips make electrical contact with the fluid/product and thus an electrical connection is made between the probes 2 when the fluid/product is flowing through the pipe 1.

For FIGS. 8-9, the probes 2 are mounted to a pipe (no pipe is connected in FIG. 8, but is connected to the system in FIG. 9) through a section of the pipe 1 with two holes drilled 180 degrees apart such that the probes may be mounted using a compression bracket 80. FIG. 8 illustrates the probes 2 connected with the compression bracket and FIG. 9 illustrates the compression bracket with sensors connected with the pipe. As illustrated, the probes are able to access a interior cavity 70 of the pipe 1 and are opposing each other.

What is claimed is:

1. A method comprising:
   providing a product into a first end of a conduit so that the product flows toward a second end of the conduit, wherein the conduit comprises an interior cavity, a first set of probes attached at a first location and a second set of probes at a second location, the first and second locations being separate from each other and being between the first and second ends;
   monitoring the conductivity of the product flowing in the conduit at the first location using current measured between the first set of probes;
   monitoring the conductivity of the product flowing in the conduit at the second location using current measured between the second set of probes;
   introducing a marker material into an entry port so that the marker material flows with the product toward the second end, the marker material comprising a conductivity that is substantially different than the conductivity of the product;
   detecting, at a first time, that the product conductivity determined at the first set of probes at the first location has changed due to the introduction of the marker material; and
   detecting, at a second time, that the product conductivity determined at the second set of probes at the second location has changed due to the introduction of the marker material.

2. The method of claim 1, further comprising determining a residence time by subtracting the second time from the first time resulting in a time it takes the marker material to flow from the first location to the second location.

3. The method of claim 1, wherein the introduced marker material comprises an injection fluid.

4. The method of claim 1, wherein the introduced marker material comprises a volumetric source of thermal energy comprising one of microwave, ohmic or radio frequency heating energy.

5. The method of claim 1, wherein the introduced marker material comprises particulate food or biomaterial pretreated to increase its conductivity.

6. The method of claim 1, wherein the introduced marker material comprises a simulated particulate food or biomaterial fabricated from an insulating material to minimize its conductivity.

7. The method of claim 1, wherein the marker material is introduced so that the marker material mixes with the product to form a combined material.

8. The method of claim 7, wherein the detecting, at a first time, that the conductivity at the first set of probes at the first location has changed comprises detecting, at the first time, the conductivity of the combined material at the first set of probes at the first location, and wherein the detecting, at a second time, that the conductivity at the first set of probes at the second location has changed comprises detecting, at the second time, the conductivity of the combined material at the second set of probes at the second location.

9. The method of claim 1, further comprising monitoring the conductivity of the product flowing in the conduit at a third location using a third set of probes; and detecting, at a third time, that the material conductivity at the third set of probes at the third location has changed due to the introduction of the marker material.

10. A system comprising:
a conduit for carrying a product, the conduit comprising
a first end;
a second end;
a body defining a first set of apertures at a first location and a second set of apertures at a second location, wherein the first and second locations are separate locations and are in between the first and second ends;
an interior cavity configured to receive the product so that the product flows from the first end toward the second end; and
an introduction port for receiving a marker material which is configured to flow with the product when introduced,
a first set of probes disposed in the first set of apertures at the first location, wherein the first set of probes is configured to measure conductivity of the product located at the first location, wherein the first set of probes is further configured to detect, at a first time, that the conductivity at the first location has changed due to the introduction of the marker material; and
a second set of probes disposed in the second set of apertures at the second location, wherein the second set of probes is configured to measure conductivity of material located at the second location, wherein the second set of probes is further configured to detect, at a second time, that the conductivity at the second location has changed due to the introduction of the marker material.

11. The system of claim 10, further comprising a computing device that is configured to:
record the first and second times; and
calculate a residence time by determining the difference between the first and second times.

12. The system of claim 10,
wherein the first set of probes comprises a first probe and a second probe and the second set of probes comprises a third probe and a fourth probe,
wherein the first probe and second probe are disposed in the conduit opposite of each other at the first location so that a first tip of the first probe opposes a second tip of the second probe;
wherein the third probe and fourth probe are disposed in the conduit opposite of each other so that a third tip of the third probe opposes a fourth tip of the fourth probe.

13. The system of claim 12, wherein the first tip of the first probe receives a current outputted by the second tip of the second probe, and an amount of current received at the first tip is measured, and wherein the conductivity of the product is directly proportional to the measured current.

14. The system of claim 10, wherein the first set of probes comprises a first probe and a second probe; wherein the first and second probes are opposingly disposed in the conduit so that the first probe and second probe face each other and are both disposed in a plane that is perpendicular to a longitudinal axis of the conduit.

15. The system of claim 10, wherein the conduit further comprises an interior wall and an insulating layer covering the interior wall so that the first set of probes is electrically insulated from the interior wall.

16. A method comprising:
providing a food product into a first end of a conduit so that the food product flows toward a second end of the conduit, wherein the conduit comprises an interior cavity, a first set of probes attached at a first location disposed in a plane that is perpendicular to a longitudinal axis of the conduit and a second set of probes at a second location disposed in a plane that is perpendicular to a longitudinal axis of the conduit, the first and second locations being separate from each other and being between the first and second ends;
monitoring the conductivity of the food product flowing in the conduit at the first location using current measured between the first set of probes;
monitoring the conductivity of the food product flowing in the conduit at the second location using current measured between the second set of probes;
introducing a marker material into an entry port, the marker material comprising a conductivity that is substantially different than a conductivity of the food product; and
detecting a conductivity of material located at one or both of the first location and the second location with one or both of the first set of probes and the second set of probes.

17. The method of claim 16, wherein each of the first and second set of probes are spaced from each other along a length of the conduit, wherein the conduit comprises a pipe, wherein the first set of probes oppose each other and are orientated radially about the pipe at a first radial position, and wherein the second set of probes oppose each other and are orientated radially about the pipe at a second radial position, wherein the first radial position is different from the second radial position, wherein homogeneity of the food product is determined based on a conductivity of the food product measured at the first set of probes and a conductivity of the food product measured at the second set of probes.

18. The method of claim 17, wherein the determining the homogeneity of the food product comprises measuring the conductivity of the food product across a first cross-section of the pipe at the first set of probes and measuring the conductivity of the food product across a second cross-section of the pipe at the second set of probes.

* * * * *